_United States Patent_ [19]

Bernstein

[11] 4,250,164

[45] Feb. 10, 1981

[54] METHOD OF TREATING PSORIASIS OF THE NAILS AND COMPOSITION

[76] Inventor: Joel E. Bernstein, 615 Brierhill Rd., Deerfield, Ill. 60015

[21] Appl. No.: 28,092

[22] Filed: Apr. 9, 1979

[51] Int. Cl.³ .................... A61K 7/04; A61K 31/58
[52] U.S. Cl. ............................ 424/61; 424/238; 424/241
[58] Field of Search .................... 424/61, 238, 241

[56] References Cited

U.S. PATENT DOCUMENTS 2,799,613   7/1957   Blodorn ............................ 424/61
3,482,018   12/1969  Szabo et al. ....................... 424/238

OTHER PUBLICATIONS

Modern Drug Encyclopedia, (1975), pp. 17 and 27.

Primary Examiner—Elbert L. Roberts
Attorney, Agent, or Firm—Vogel, Dithmar, Stotland, Stratman & Levy

[57] ABSTRACT

An improved method of treating psoriasis of the nails comprising applying nail polish containing an antipsoriasis effective amount of a topical steroid effective against psoriasis therein and composition useful in said method.

8 Claims, No Drawings

METHOD OF TREATING PSORIASIS OF THE NAILS AND COMPOSITION

BACKGROUND OF THE INVENTION

Psoriasis is a chronic relapsing papulosquamous skin disease which can also affect nails. Nail involvement resembles a fungus infection with stippling, separation of the distal margin, nail loss, scales under the nail plate, thickening and discoloration and is seen in anywhere from ten to fifty percent of psoriasis patients.

While there are a limited number of effective anti-psoriasis agents, it is far more difficult to treat psoriasis of the nails than that of the skin.

Treatment of psoriasis (skin) can include daily removal of the scales by applying soap and water and scrubbing gently with a soft brush, followed by the application of a keratolytic ointment.

Topical steroids, particularly 0.01 to 0.025% of fluocinolene acetonide, 0.25% fluorandrenolide and 0.05% triamcinolene acetonide creams have replaced many previous local treatments. The topical steroids are most effective if covered with a polyethylene film, Saran Wrap ™ or HandiWrap ®, which preferably are sealed with tape. Thin polyethylene gloves are used for treating the hands and fingers.

Another method involving topical steroids are the use of an inconspicuous, transparent, plastic surgical tape containing fluorandrenolide, Cordran ® tape sold by Dista Products Company, Division of Eli Lilly and Company, Indianapolis, Indiana 46206.

Generally speaking, while there are methods which are effective in treating psoriasis of the skin, attempts to treat nail involvement have failed miserably. Topically applied steroids are generally without effect.

I have found that excellent results are obtained when the topical steroid is applied to the affected nails in nail polish.

SUMMARY OF THE DISCLOSURE

Psoriasis of the nails is treated by periodically applying nail polish containing an effective amount of a topically active steroid to the affected nails.

DETAILED DESCRIPTION OF THE PREFERRED EMBODIMENTS

In the practice of the present invention, topical steroids such as betamethhasone valerate is sold under the trademark Valisone ® by Schering Corporation, Galloping Hill Road, Kenilworth, New Jersey 07033. Valisone is available in aerosol 0.15% w/w reduced strength cream (0.01%) and 0.1% cream, ointment and lotion. In the practice of the present invention, when Valisone is used as the topical steroid, it is preferred to use the 0.1% lotion which contains in each gram betamethasone valerate equivalent to 1.0 mg. of betamethasone (9-fluoro-11$\beta$, 17,21-trihydroxy-16$\beta$-methyl-pregna-1,4-diene-3,20-diene 17 valerate) in a vehicle consisting of isopropyl alcohol (47.5%) and water slightly thickened with carboxy vinyl polymer, the pH adjusted to approximately 4.7 with sodium hydroxide.

Betamethasone valerate is effective in relieving the inflammatory manifestations of corticoid-responsive dermatoses because of its anti-inflammatory, antipruretic and vasoconstrictive actions.

Fluorondrenolide (6$\alpha$-fluoro-16$\alpha$-hydroxycortisone 16,17-acetonide) is sold by Dista Products Company, Division of Eli Lilly and Company, P. O. Box 1407, Indianapolis, Indiana 46206 and is available as a cream, ointment or lotion in full (0.05%) or half (0.025%) preparations. Gordran also is primarily effective as a topical corticosteroid because of its anti-flammatory, antipruretic and vasoconstrictive actions.

Generally speaking, in the practice of the present invention, a topically effective corticosteroid having anti-inflammatory, anti-pruretic and vasoconstrictive actions, preferably in lotion form, is mixed with commercially available nail polish such as Revlon clear nail polish in an anti-psoriasis effective amount, preferably in a 50:50 mixture and said mixture is periodically applied to the affected nails preferably at least once daily and more often in severe, intractable cases.

The following examples further illustrate the present invention.

EXAMPLE 1

A nail polish composition useful in treating psoriatic nails was prepared by mixing 0.1% Valisone lotion with Revlon clear nail polish in a 50:50 mixture.

EXAMPLE 2

The composition of Example 1 was applied twice daily to the nails of a 36 year old male psoriasis patient with psoriatic nail involvement with noticeable improvement after 8 weeks.

EXAMPLE 3

The composition of Example 1 was applied twice daily to the psoriatic nails of a 50 year old patient. There was complete clearing of the nail involvement within eight weeks.

EXAMPLE 4

The composition of Example 1 was applied once daily to a 55 year old female patient with psoriatic nails with noticeable improvement after 6 weeks.

EXAMPLE 5

A nail polish composition was prepared as in Example 1, using 0.05% Cordran lotion instead of Valisone lotion. The composition was applied to the psoriatic nails of psoriasis patients with similar results to Examples 2-4.

It will be understood by those skilled in the art that any commercial nail polish, colored or clear, can be used in the practice of the invention and while Cordran and Valisone lotions have been used by way of example, any topical steroid having anti-inflammatory, antipruretic and vasoconstrictive activities normally used in the treatment of psoriasis can be employed in the practice of this invention.

I claim:

1. A method of treating psoriatic nails comprising periodically applying to said psoriatic nails nail polish containing an effective amount of a topically active corticosteroid effective against psoriasis.

2. The method of claim 1 wherein said topical steroid is a fluorinated corticosteroid.

3. A method of treating psoriatic nails comprising periodically applying to said psoriatic nails nail polish containing an effective amount of fluorinated corticosteroid selected from the group consisting of betamethasone valerate and fluorandrenolide.

4. The method of claim 3 wherein said corticosteroid is 0.1% betamethasone valerate lotion.

5. The method of claim 3 wherein said corticosteroid is 0.05% fluorandrenolide lotion.

6. An antipsoriatic nail polish composition comprising nail polish containing an effective amount of a topically active corticosteroid effective against psoriasis.

7. The composition of claim 6 wherein said corticosteroid comprises 50% by volume of said composition.

8. The composition of claim 6 wherein said steroid is selected from the group consisting of fluorandrenolide or betamethasone valerate.

* * * * *